(12) United States Patent
Welter et al.

(10) Patent No.: US 12,319,604 B2
(45) Date of Patent: Jun. 3, 2025

(54) DEVICE FOR PURIFYING DRINKING WATER IN MULTIPLE STAGES

(71) Applicant: instrAction GmbH, Heidelberg (DE)

(72) Inventors: Martin Welter, Neckargemünd (DE); Christian Meyer, Schwetzingen (DE); Kristian Lungfiel, Wiesbaden (DE)

(73) Assignee: INSTRACTION GMBH, Heidelberg (DE)

( * ) Notice: Subject to any disclaimer, the term of this patent is extended or adjusted under 35 U.S.C. 154(b) by 722 days.

(21) Appl. No.: 17/273,625

(22) PCT Filed: Sep. 9, 2019

(86) PCT No.: PCT/EP2019/073952
§ 371 (c)(1),
(2) Date: Mar. 4, 2021

(87) PCT Pub. No.: WO2020/049184
PCT Pub. Date: Mar. 12, 2020

(65) Prior Publication Data
US 2021/0317027 A1    Oct. 14, 2021

(30) Foreign Application Priority Data
Sep. 7, 2018   (DE) .................... 10 2018 121 904.0

(51) Int. Cl.
*C02F 9/20* (2023.01)
*A01N 25/04* (2006.01)
(Continued)

(52) U.S. Cl.
CPC ............... *C02F 9/20* (2023.01); *A01N 25/04* (2013.01); *A61L 2/10* (2013.01); *A61L 2/235* (2013.01);
(Continued)

(58) Field of Classification Search
None
See application file for complete search history.

(56) References Cited

U.S. PATENT DOCUMENTS 3,828,930 A * 8/1974 Eimer .................... B01D 21/34
                                                210/405
3,950,251 A * 4/1976 Hiller ..................... B01D 27/02
                                                210/287
(Continued)

FOREIGN PATENT DOCUMENTS

CH         339888 A    7/1959
CN     107619127 A    1/2018
(Continued)

OTHER PUBLICATIONS

International Search Report and Written Opinion for International Application No. PCT/EP2019/073952, dated Nov. 29, 2019, 9 pages.

*Primary Examiner* — Chester T Barry
(74) *Attorney, Agent, or Firm* — Buchanan Ingersoll & Rooney PC

(57) ABSTRACT

A device for purifying drinking water in multiple stages by combining orthogonal purification technologies in one module is described, where the device comprises a housing, a water inlet opening, a water outlet opening, a hollow cylinder which is filled with activated carbon, and a hollow cylinder with a semipermeable wall, wherein the hollow cylinder contains a chelating bactericidal gel or a chelating and bactericidal gel for removing heavy metals or bacteria or for removing heavy metals and bacteria.

11 Claims, 8 Drawing Sheets

(51) Int. Cl.

| | | |
|---|---|---|
| *A61L 2/10* | (2006.01) | |
| *A61L 2/235* | (2006.01) | |
| *A61L 2/24* | (2006.01) | |
| *B01D 61/14* | (2006.01) | |
| *B01D 69/08* | (2006.01) | |
| *B01J 20/20* | (2006.01) | |
| *B01J 20/28* | (2006.01) | |
| *B01J 45/00* | (2006.01) | |
| *B01J 47/022* | (2017.01) | |
| *B01J 47/12* | (2017.01) | |
| *B01J 49/85* | (2017.01) | |
| *C02F 1/00* | (2023.01) | |
| *A61L 101/46* | (2006.01) | |
| *C02F 1/28* | (2023.01) | |
| *C02F 1/44* | (2023.01) | |
| *C02F 1/50* | (2023.01) | |
| *C02F 101/20* | (2006.01) | |

(52) U.S. Cl.
CPC ............. *A61L 2/24* (2013.01); *B01D 61/145* (2013.01); *B01D 69/08* (2013.01); *B01J 20/20* (2013.01); *B01J 20/28052* (2013.01); *B01J 45/00* (2013.01); *B01J 47/022* (2013.01); *B01J 47/12* (2013.01); *B01J 49/85* (2017.01); *C02F 1/008* (2013.01); *A61L 2101/46* (2020.08); *A61L 2202/11* (2013.01); *A61L 2202/14* (2013.01); *B01D 2311/2626* (2013.01); *B01D 2311/2692* (2013.01); *C02F 1/283* (2013.01); *C02F 1/444* (2013.01); *C02F 1/50* (2013.01); *C02F 2101/20* (2013.01); *C02F 2201/003* (2013.01); *C02F 2201/006* (2013.01); *C02F 2209/05* (2013.01); *C02F 2209/06* (2013.01); *C02F 2303/04* (2013.01)

(56) References Cited

U.S. PATENT DOCUMENTS

| | | | | |
|---|---|---|---|---|
| 4,540,489 A | * | 9/1985 | Barnard | C02F 1/003 210/287 |
| 4,575,330 A | * | 3/1986 | Hull | G03F 7/0037 430/269 |
| 4,775,258 A | * | 10/1988 | Lange | E04B 1/1906 403/171 |
| 4,828,698 A | * | 5/1989 | Jewell | B01D 27/02 210/321.86 |
| 5,288,540 A | | 2/1994 | Albrinck et al. | |
| 7,081,201 B2 | * | 7/2006 | Bassett | B01D 61/20 210/493.1 |
| 7,135,155 B1 | * | 11/2006 | Long, Jr. | B01J 19/26 422/224 |
| 7,172,695 B2 | * | 2/2007 | Kato | C02F 1/505 210/260 |
| 7,422,121 B2 | | 9/2008 | Stadelmann | |
| 2005/0035041 A1 | * | 2/2005 | Nohren | C02F 1/002 210/321.89 |
| 2006/0157416 A1 | * | 7/2006 | Seidel | C02F 1/288 210/688 |
| 2018/0147776 A1 | | 5/2018 | Kotani | |
| 2019/0039917 A1 | | 2/2019 | Dahlberg et al. | |
| 2020/0171463 A1 | | 6/2020 | Meyer et al. | |
| 2020/0189946 A1 | * | 6/2020 | Sin | C02F 3/105 |
| 2020/0197908 A1 | | 6/2020 | Welter et al. | |

FOREIGN PATENT DOCUMENTS

| | | | | |
|---|---|---|---|---|
| DE | 3001674 A1 | | 7/1981 | |
| DE | 3787659 T2 | | 2/1994 | |
| DE | 10217649 A1 | | 1/2004 | |
| DE | 202016100447 U1 | | 5/2017 | |
| DE | 102016107485 A1 | | 10/2017 | |
| DE | 202018100396 U1 | | 2/2018 | |
| DE | 202018101926 U1 | | 5/2018 | |
| DE | 102017007273 A1 | * | 2/2019 | ............ A01N 25/34 |
| JP | 2007-152188 A | | 6/2007 | |
| JP | 2015024364 A | * | 2/2015 | |
| KR | 930000264 A | | 1/1993 | |
| RU | 2221641 C2 | | 1/2004 | |
| RU | 42817 U1 | | 12/2004 | |
| RU | 87365 U1 | | 10/2009 | |
| RU | 114680 U1 | | 4/2012 | |
| SU | 916443 A1 | | 3/1982 | |
| WO | 91/19675 A1 | | 12/1991 | |
| WO | 2016030021 A1 | | 3/2016 | |
| WO | 2017/018525 A1 | | 2/2017 | |
| WO | 2017/209025 A1 | | 12/2017 | |

* cited by examiner

DEVICE FOR PURIFYING DRINKING WATER IN MULTIPLE STAGES

CROSS-REFERENCE TO RELATED APPLICATIONS

This application is the national phase of International Application No. PCT/EP2019/073952, filed 9 Sep. 2019, which claims priority to German Application No. 10 2018 121 904.0, filed 7 Sep. 2018. The disclosure of each of these applications is incorporated herein by reference in its entirety for all purposes.

FIELD OF THE INVENTION

The present invention relates to a device in which at least two water purification processes are combined in one unit, wherein one process comprises a chelating gel and/or a bactericidal gel for removing heavy metals and/or bacteria.

BACKGROUND OF THE INVENTION

A large number of appliances, which follow and in some cases already combine different strategies and techniques, are available on the market for drinking water purification.

In addition to the dominant technique of reverse osmosis which has the largest market share, there are a large number of appliances which use different filtration techniques or distillation processes.

All known processes have (sometimes serious) disadvantages:

In the case of reverse osmosis, the greatest disadvantage is the low yield of drinking water, which rarely exceeds 10% of the water volume used, is energy-intensive and also removes health-promoting elements, such as magnesium, from the drinking water. This is sometimes added to the drinking water again in a complex manner in a second step.

The disadvantage of extremely high energy consumption is common to distillation processes. Moreover, there, as in the case of reverse osmosis, the health-promoting elements are also removed, with the result that distilled water forms which is not suitable for long-term consumption, and important ingredients such as magnesium salts must again be replenished in a subsequent step.

The water purification machines which combine several filtering techniques in separate units/cartridges require complex piping with corresponding valves or connectors, which are by their nature susceptible to faults and open up the possibility of leaks, etc. Moreover, connections are places where bacteria, etc. have particularly good opportunities to grow because of the flow conditions.

Compared with the above-mentioned RO technique and distillation processes, many purification methods which are based on filtration (or on a combination of different, orthogonal filtration techniques) operate, as a rule, with a high (100%) yield and with line pressure, resulting in no additional energy consumption. The prerequisite for this, however, is a setup with a low pressure drop in the apparatus and the use of coarse-grained absorber resins, which reduce the effectiveness of the depletion and the productivity.

A known filter medium utilized on the market is e.g. activated carbon, which is used as a packed bed of particles in cartridges with linear throughflow or as a pressed hollow cylinder with radial throughflow. From the point of view of the productivity and the pressure drop, the hollow cylinder represents the ideal setup.

Other known media are the MetCap® resin (WO2016030021) for removing heavy metals from drinking water and the BacCap® resin (DE102017007273A1) for removing bacteria from drinking water. Both are usually used in cartridges and sometimes combined.

The MetCap resins are a linear polyvinylamine which is applied to a porous particle and then reacted with a bifunctional crosslinker to form a three-dimensional polymeric network. This network has numerous amino groups with a high density and can, through the formation of very stable metal-amine complexes, bind heavy metals out of high-capacity solutions in a chelating manner and thus remove them. For heavy metals which form only weak amine complexes (e.g. nickel, manganese), further chelating groups can be introduced into the polymeric network, e.g. carboxylates, thiols, etc.

The BacCap resins are likewise amino polymers which are produced in a similar manner to the MetCap absorbers. However, the blend, stoichiometry, degree of crosslinking, etc. is optimized for an antibacterial action. The antibacterial action is in all probability due to the interaction between the at least partially protonated (and thus positively charged) amino groups of the polymer and the negatively polarized bacterial cell envelope. One possible explanation is a direct interaction of the polymeric amino groups with the fatty acids of the cell envelope, which is damaged as a result. A second explanation could be the blocking of the ion channels in the cell walls by the amino polymer. In the final analysis, both explanations result in the destruction or damage of the cell membrane and ultimately in the bacteria dying off.

It is particularly important here to point out that neither for removing the bacteria nor for binding the heavy metals are substances released into the drinking water. In that respect the proposed process clearly differs from others which release silver, chlorine or other substances into the drinking water and contaminate it.

A further advantage of the proposed device is revealed by the easy handling. In contrast to filtration processes such as reverse osmosis, a pressure increase by means of a pump, which in turn requires electricity, is not necessary. The same applies to UV systems on the market, which also require power during operation.

A third process for purifying drinking water is filtration by micro- and nanofiltration processes.

A further process for treating, especially for softening, drinking water is the filtration of calcium- and magnesium-containing drinking water via ion exchangers. In the process, calcium and magnesium are bound and, for this, in each case two molar equivalents of sodium are released into the drinking water. The process has come under criticism because of the negative effects of too much sodium on the cardiovascular system. A disadvantage of this process is, in addition, the low capacity and the need for frequent replacement or regeneration. Moreover, these appliances tend towards microbial contamination.

In marked contrast to the three first-named filter media, the filtration capacity of the ion exchanger is exhausted by far the quickest. When hard water is used, a replacement or regeneration of the resin is necessary after only a few days, but at the latest after one to two weeks with normal use.

Cartridges, filled with heavy metal-absorbing resins (e.g. "MetCap®"), bacteria-removing resins (e.g. "BacCap®"), activated carbon or also the filtration membranes have a lifetime of approx. 6 months. It is not uncommon that these elements have to be replaced as a precaution before they are technically exhausted.

In addition to the above-described devices, there is a whole range of appliances that are on the market or protected, which combine the individual purification techniques with each other in a modular manner.

These appliances have the advantage that individual customers can, depending on the nature and contamination of their drinking water, which can contain very different contaminants in different concentrations according to region, replace the respective purification cartridges individually when they are exhausted. A disadvantage is that, in order to monitor the capacity of each individual cartridge, sensors have to be installed which individually issue messages when parts of the system are exhausted. Alternatively, manufacturers issue protocols which specify particular periods of time in which to change the individual cartridges.

The process is complex and not consumer-friendly. There is a danger that the complex protocols or maintenance periods will not be adhered to and the drinking water quality is on average more likely to suffer than improve.

DE202018101926U1 discloses a two-part filter device for the purification of water in aircraft. The published document describes an outer hollow cylinder made of activated carbon with membranes (especially hollow filter membranes) on the inside. The water to be filtered is introduced into the activated carbon laterally, filtered through it and finally reaches the interior of the activated carbon hollow cylinder. The pore size of the activated carbon is preferably 0.5 µm. The pore size of the internal membrane is preferably in a region around 0.2 µm. These relatively large pores were chosen in order to keep the back pressure of the system low. The authors assert that they can retain bacteria and heavy metals with the device claimed by them.

It is known that membranes, especially hollow fibre membranes for water filtration, are used in a broad range. For removing bacteria, as a rule membranes with a pore size of 0.02 µm (20 nm) are used, since larger pore sizes do not retain bacteria and other microbes (in particular viruses). A clear pressure increase is accepted in order to ensure the bacteria retention. The 200 nm proposed in the present published document clearly lie above the usual 20 nm. A significant bacteria retention thus seems to be very unlikely. Presumably, the large pore size was chosen for reasons of back pressure minimization.

The specified example of lo7 depletion is demonstrated using *Brevundimonas diminuta*. This microbe is not listed in any drinking water ordinance and is rather an exotic microbe. Usually *E. coli* or *Pseudomonas aeruginosa* are used as test organism.

The activated carbon itself is largely unsuitable as bacteria retention. Admittedly, with sufficiently small pores bacteria are initially retained. However, this is already doubtful due to the pore size of 0.5 µm of the activated carbon. Subsequently, the bacteria grow in the activated carbon and are then released into the water, whereby this is contaminated. With that said, a second purification stage certainly makes sense. There, however, if the pores are chosen to be as large, as indicated above, an effective filtration appears very doubtful.

The same applies to the removal of heavy metals. Heavy metals are not removed at all by activated carbon or only in a very small proportion with very low capacity. Heavy metals are certainly not stopped by ultrafiltration membranes. For this, membranes with pore sizes in the single-figure nanometer range are required, which are unsuitable for the intended application due to their high pressure drop.

In contrast to the device merely with a combination of activated carbon and membrane filtration specified in DE202018101926U1, in the present patent specification a combination with absorber gels developed specifically for drinking water purification is proposed. Specifically, the chelating absorber gel developed by instrAction binds heavy metals effectively, quickly and with high capacity. This performance cannot be achieved by simple membrane filtration. At the same time, the particles with an antibacterial action effectively remove microbes that are relevant to drinking water, in particular bacteria, by filtration in the proposed setup—in contrast to activated carbon, which is more likely to be considered a source of bacteria, and filter membranes with a pore size that is too large.

In DE10217649A1 a process is presented in which a noble metal surface is treated such that, as soon as it comes into contact with water, it releases metal ions into the water which for their part then kill bacteria. Silver, among others, is proposed as preferred noble metal. The principle of action is thus based on the release of antibacterial substances. It is thus similar to the silver treatment of ion exchangers for the same purpose, which is criticized. The release of metals that are potentially harmful to health is inherent in this process. Furthermore, the emergence of silver-resistant microbes is regarded as a disadvantage. Heavy metals are not removed using this process, on the contrary: in the end, there are more heavy metals in the filtrate (according to the invention) than before.

The present invention is based on the interaction of the bacteria with the particle surface in the proposed device and not on the release of heavy metal ions with an antibacterial action into the drinking water. Through the proposed process, not only are bacteria and other microbes effectively filtered out of the drinking water, but in addition heavy metals are also removed.

CH339888A proposes a filter candle consisting of an activated carbon packed bed with an inner central drain for water purification. The activated carbon here is "combined or impregnated" with "oligodynamically active substances", such as silver or copper or the salts of these metals. These substances reliably kill bacteria. As a result, microbes are to be prevented from growing through the activated carbon and bacteria are to be prevented from contaminating the filtered water. This danger is the key point of criticism regarding the use of activated carbon in water purification. The whole device is substantially used to remove "chlorine" and other negative taste producing substances via absorption. The device as such has in the meantime been further developed and today generally goes on sale as pressed activated carbon. The invention proposed in CH339888A has the serious disadvantage that toxic heavy metals such as silver and copper are released into the filtrate.

As shown above, this serious disadvantage does not apply when the present invention is used: in the described device according to the invention, bacteria are removed by interaction with the particle surface of the antibacterial resin. Substances, in particular heavy metals, are not released into the filtrate in the process. On the contrary, heavy metals are removed by the filtration of the water through the chelating resin.

DE3001674A1 proposes a filter which contains activated carbon and an ion exchanger. The pH of the water to be purified is lowered to approx. pH=3 in the filter, whereby the microbial growth in the filter is to be reduced or microbes that are already present are killed. At the same time, substances with a biocidal action are released into the solution in order to kill microbes or to prevent further growth.

As in the published documents before it, it is also attempted therein to counteract the major problem of the microbially-contaminating activated carbon by releasing biocidal substances. The contamination of the filtrate with these substances that are potentially harmful to health is accepted.

These disadvantages do not occur when the device according to the invention is used, as described above.

In DE202018100396U1 a modular water purification system is described, in which two to five different purification processes are combined with each other in a modular manner. The individual purification stages each address a different group of contaminants, such as may be present in drinking water. The individual modules are independent of each other and are in contact with each other through piping. The modules are individually exchangeable and can, as soon as their capacity has been exhausted, be replaced individually. The modular setup has advantages in so far as individual components can be changed when there is a corresponding need. A disadvantage is the complex and in many respects vulnerable piping. Moreover, the removal of bacteria by simple filtration is not yet provided in DE202018100396U1.

The current proposal combines two to three of the longest-lived purification processes in one cartridge in such a way that all purification stages are concentrated in one module. This is a very space-saving and customer-friendly process, which has to monitor and replace only one cartridge, in contrast to the two to five, as proposed in DE202018100396U1. Furthermore, the processes are combined in a three-dimensional arrangement in such a way that they cause only a low back pressure; that is not planned in DE202018100396U1.

SUMMARY OF THE INVENTION

None of the published documents specified combines a rigid activated carbon hollow cylinder with a particulate packed bed consisting of chelating and antibacterial resins. Such a combination was hitherto not known in the state of the art. The same applies to the setup with a central drain over the entire module, which is likewise provided in CH339888A. There, however, only unacceptable provisions for microbe reduction are proposed. The innovative approach of multi-stage, radial filters with antibacterial resins is not provided or even only planned in any of the published documents.

DETAILED DESCRIPTION OF THE INVENTION

Figure 1:
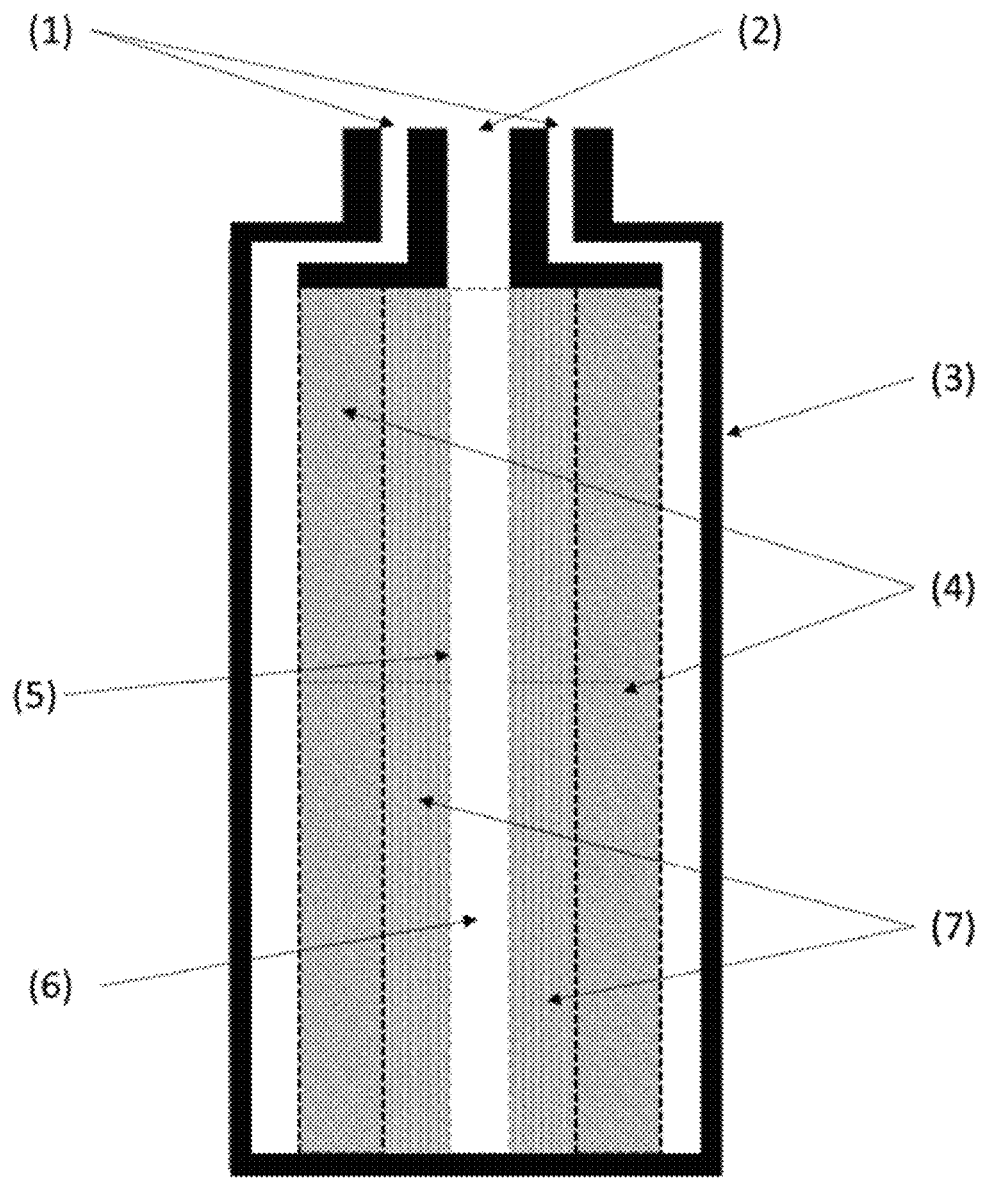
FIG. 1: Longitudinal section of the double hollow cylinder cartridge with one connection for water inlet (1), water outlet (2), housing (3), hollow cylinder made of activated carbon (4), hollow cylinder with a permeable wall (5) or hollow fibre membrane bundle (6), heavy metal-binding chelating resins and/or bacteria-removing resin (7).

The object resulting against this background is to combine the advantages of the known filtration processes in such a way that the disadvantages of the modular setup are minimized or do not even occur in the first place.

The object was achieved by a device for purifying drinking water in multiple stages by combining orthogonal purification techniques in one module, characterized in that the device comprises a housing (3), a water inlet opening (1), a water outlet opening (2), an outer hollow cylinder filled with activated carbon (4) and an inner hollow cylinder (7) with a semipermeable wall (5), wherein the inner hollow cylinder (7) with the semipermeable wall (5) comprises a chelating and/or bactericidal gel for removing heavy metals and/or bacteria.

Advantageously, the housing (3), the water inlet opening (1), the water outlet opening (2), the outer hollow cylinder (4) and the inner hollow cylinder (7) can be produced by 3D printing. This makes a cost-effective production possible and, moreover, the shape and dimensions of the device can be customized for the user.

In the claimed device, the at least two of the long-lived filtration media or techniques are combined with each other: activated carbon, a heavy metal-binding absorber resin and/or a bacteria-removing resin, as well as optionally ultrafiltration.

Figure 3:
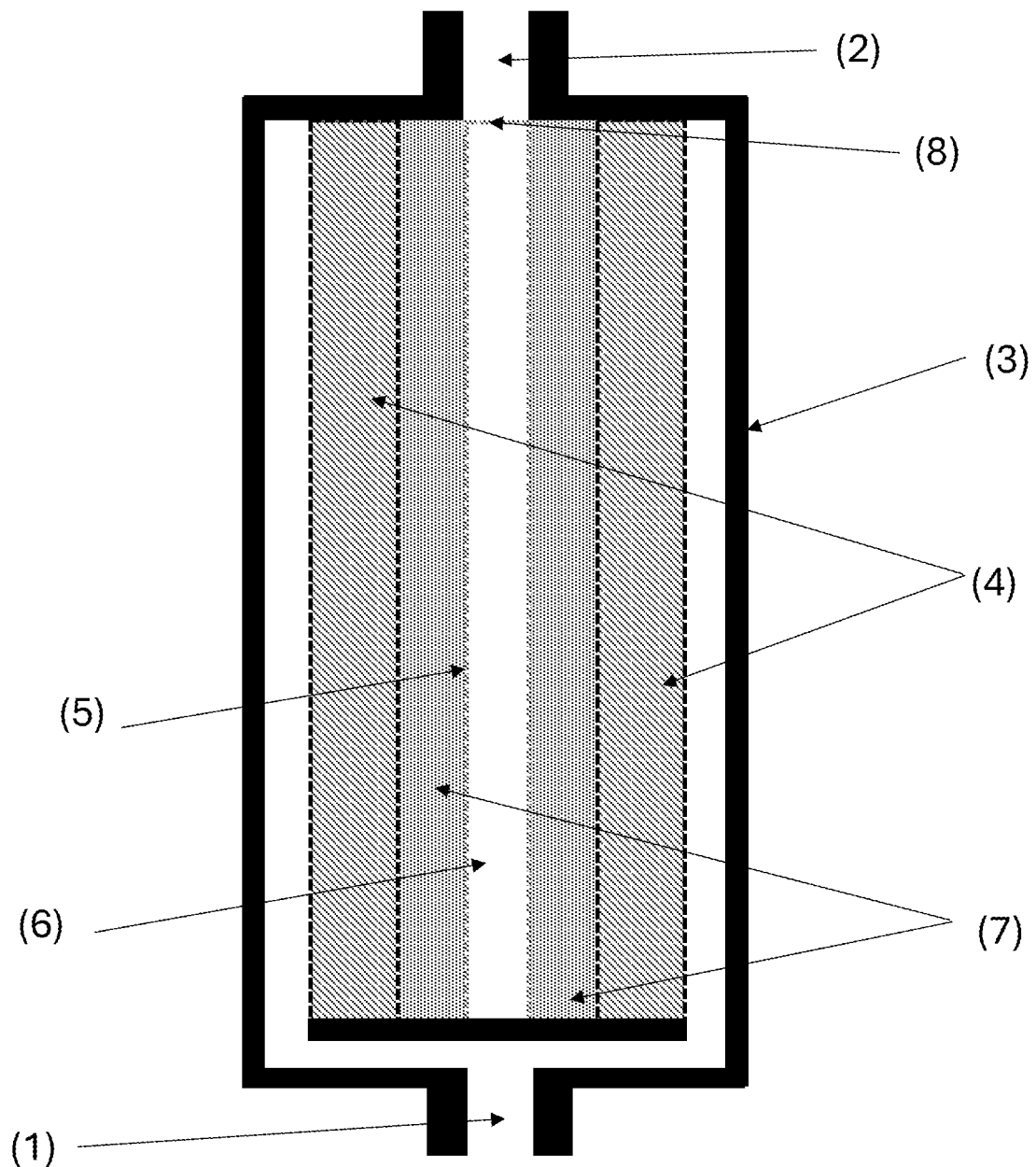
FIG. 3: Longitudinal section of the double hollow cylinder cartridge with one connection each for water inlet (1) and outlet (2) (linear structure); housing (3), hollow cylinder made of activated carbon (4), hollow cylinder with a permeable wall (5) or one or more hollow fibres (6), heavy metal-binding chelating resins and/or bacteria-removing resin as filling (7), frit (8).

This is effected by filling known outer activated carbon hollow cylinders (4) in a housing (3) with heavy metal-binding absorber resin and/or bacteria-removing resins (7) (FIG. 1, FIG. 3). Centrally, a drain in the form of a further inner hollow cylinder with a semipermeable wall (5) or a hollow fibre membrane or a bundle of hollow fibre membranes (6) is introduced, preferably over the entire length of the hollow cylinder, with the result that a total of at least two resin layers that are flowed through concentrically one after the other, with a drain placed in the middle, are presented.

In summary, the water to be filtered thus first runs through the outer activated carbon hollow cylinder, followed by the inner hollow cylinder filled with heavy metal-removing absorber resin and/or bacteria-removing resin. Finally, the water passes through the central drain, which extends over the entire length of the two hollow cylinders. This can—as third purification stage—be designed as an ultrafiltration hollow fibre membrane.

Figure 2:
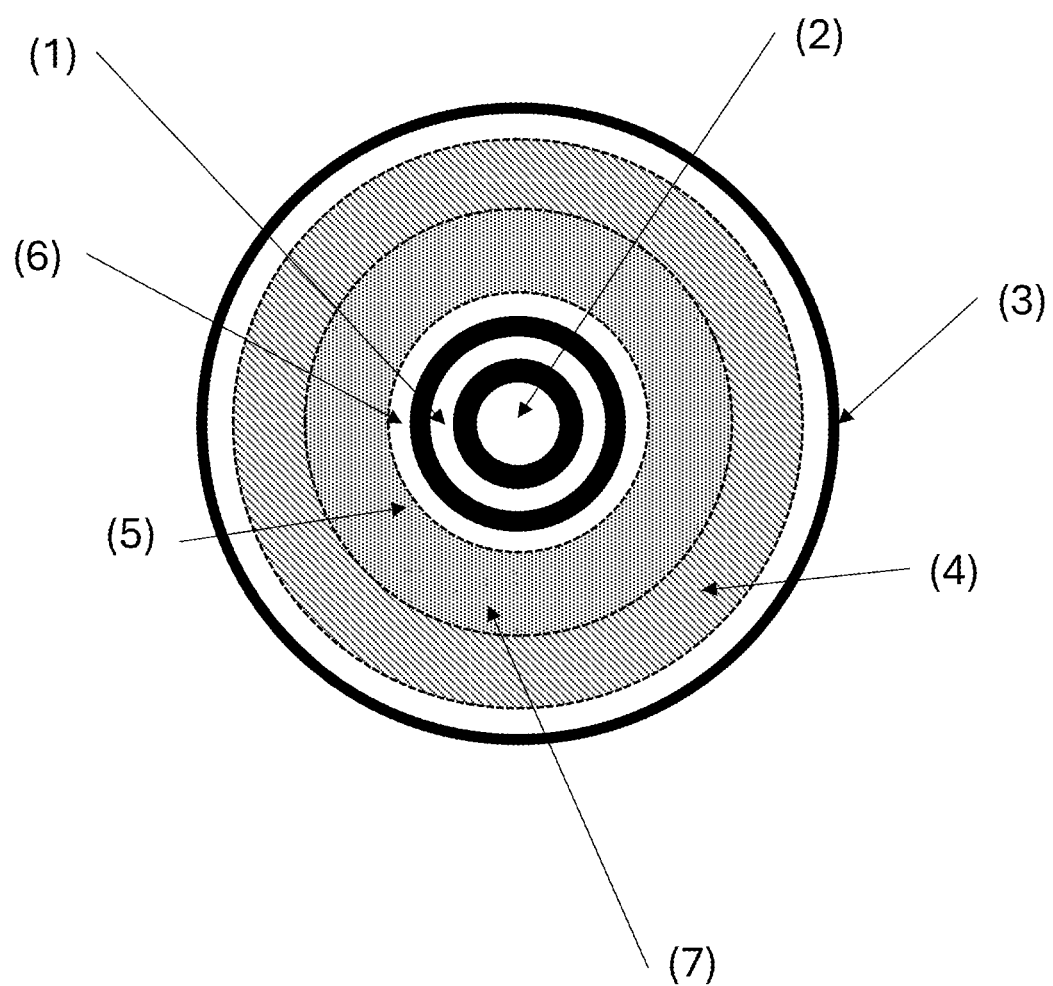
FIG. 2: Cross section of the double hollow cylinder cartridge with one connection for water inlet (1) and outlet (2); housing (3), activated carbon (4), heavy metal-binding chelating resins and/or bacteria-removing resin as filling (7), hollow cylinder with a permeable wall (5) or one or more hollow fibres (6).
Figure 4:
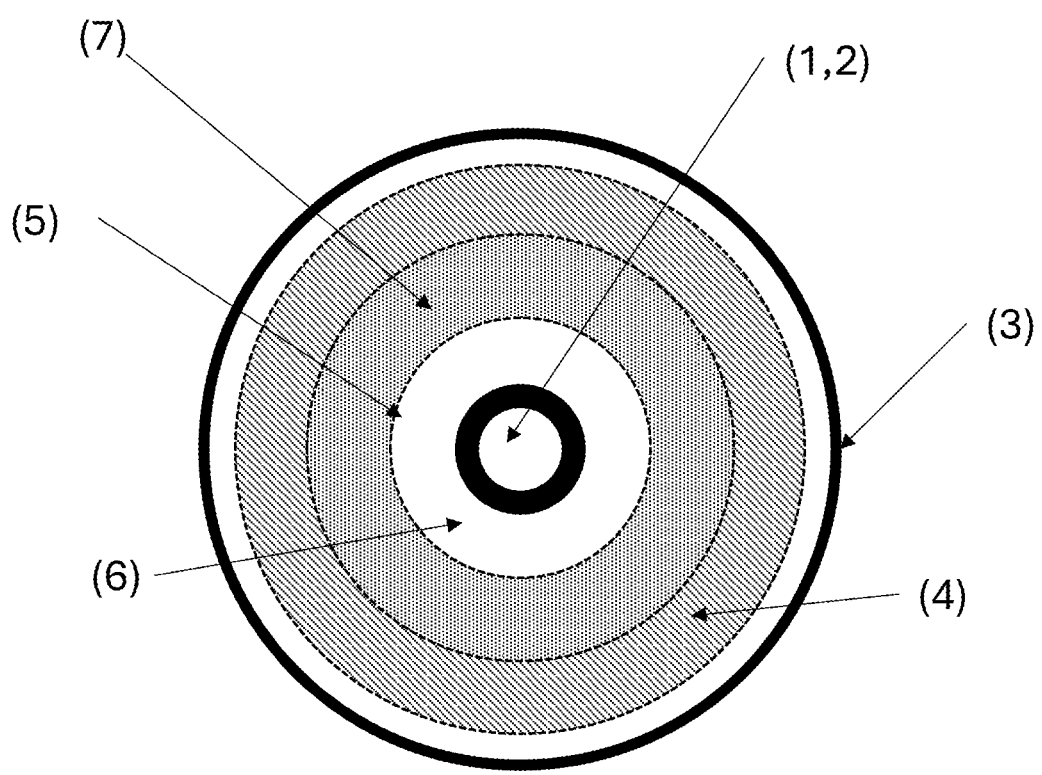
FIG. 4: Cross section of the double hollow cylinder cartridge with two connections for water inlet (1) and outlet (hidden on the opposite side), (linear structure); housing (3), activated carbon hollow cylinder (4), heavy metal-binding chelating resins and/or bacteria-removing resin as filling (7), hollow cylinder with a permeable wall (6) or one or more hollow fibres (5).

The water inlet (1) can be mounted on the same side as the water outlet (2) for easy replacement/connection to a water purification appliance (FIG. 1, FIG. 2), or opposite it for a linear installation in a pipeline (FIG. 3, FIG. 4).

The central drain (5) is essential with regard to an optimum flow through the absorber materials with a simultaneously small and uniform pressure drop over the entire filter length.

In the case of a linear flow through the filter media, an excessively high back pressure develops, which either makes an additional pump necessary or lowers the productivity in an unacceptable manner.

If particles that are too large are chosen in order to reduce the pressure, the productivity is lowered as a result of the slow exchange, the long diffusion path, between contaminated water and the binding sites within the absorber material. If bed heights that are too low are chosen and the residence time of the water in the absorber bed is thus reduced, an insufficient depletion of the contaminants results therefrom.

Figure 5:
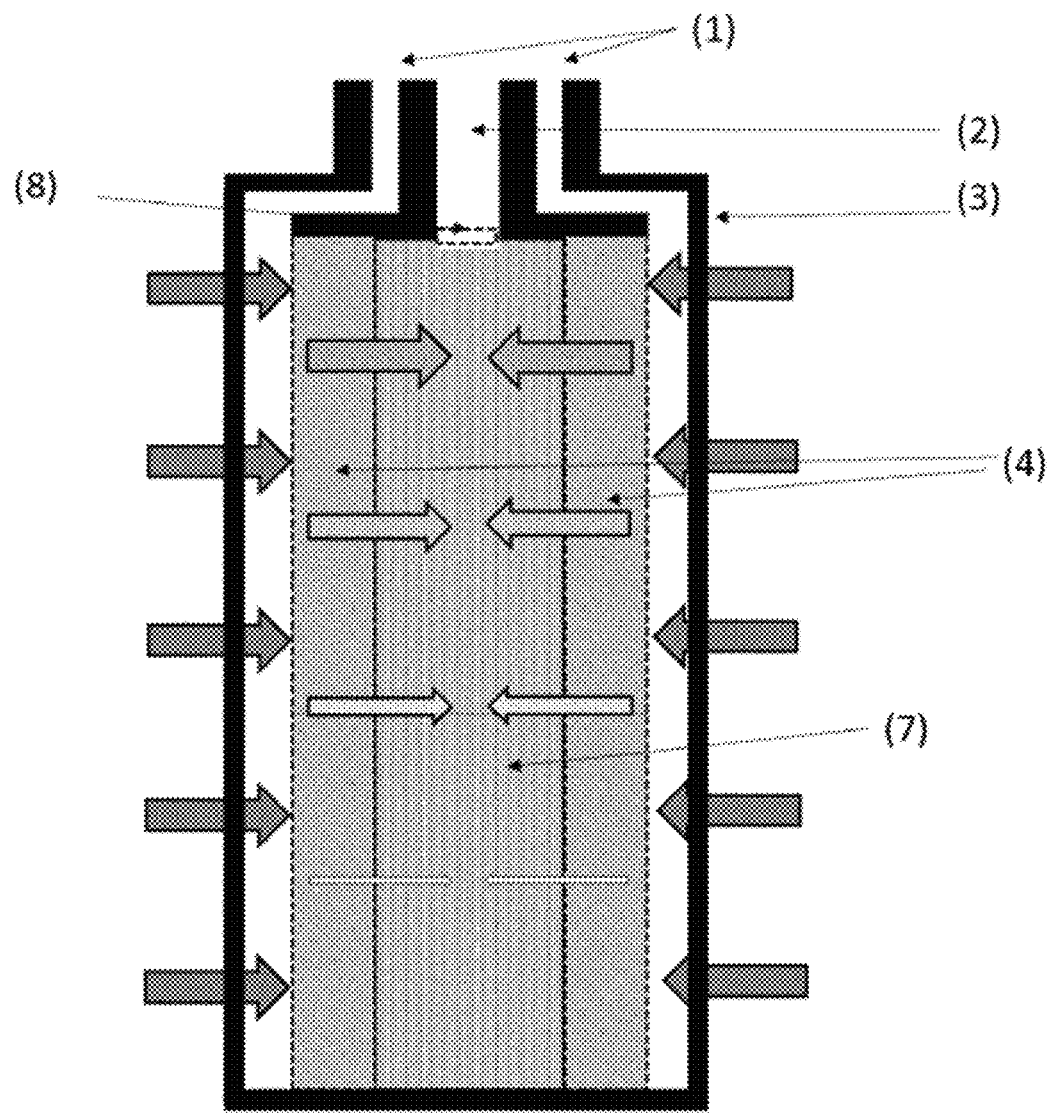
FIG. 5: Disadvantageous filtration path of the water in the case of hollow fibre cartridges filled with absorber gel without a central drain due to the lower stagnation pressure at the cartridge head (preferred flow direction indicated in the cartridge by the thickness of the arrows);water inlet (1), water outlet (2), housing (3), hollow cylinder made of activated carbon (4), heavy metal-binding chelating resins and/or bacteria-removing resin in bed form (7), frit (8).

If the inner free activated carbon hollow cylinder (5) is filled with a further absorber material (6), without the central drain claimed here, a pressure gradient is obtained over the length of the hollow cylinder which prevents a uniform flow through the gel bed (7) and leads to an insufficient depletion of the contaminants. At the latest after the capacity has been exhausted by the "shortest route", no or only an insufficient purification of the water takes place (see FIG. 5).

Figure 6:
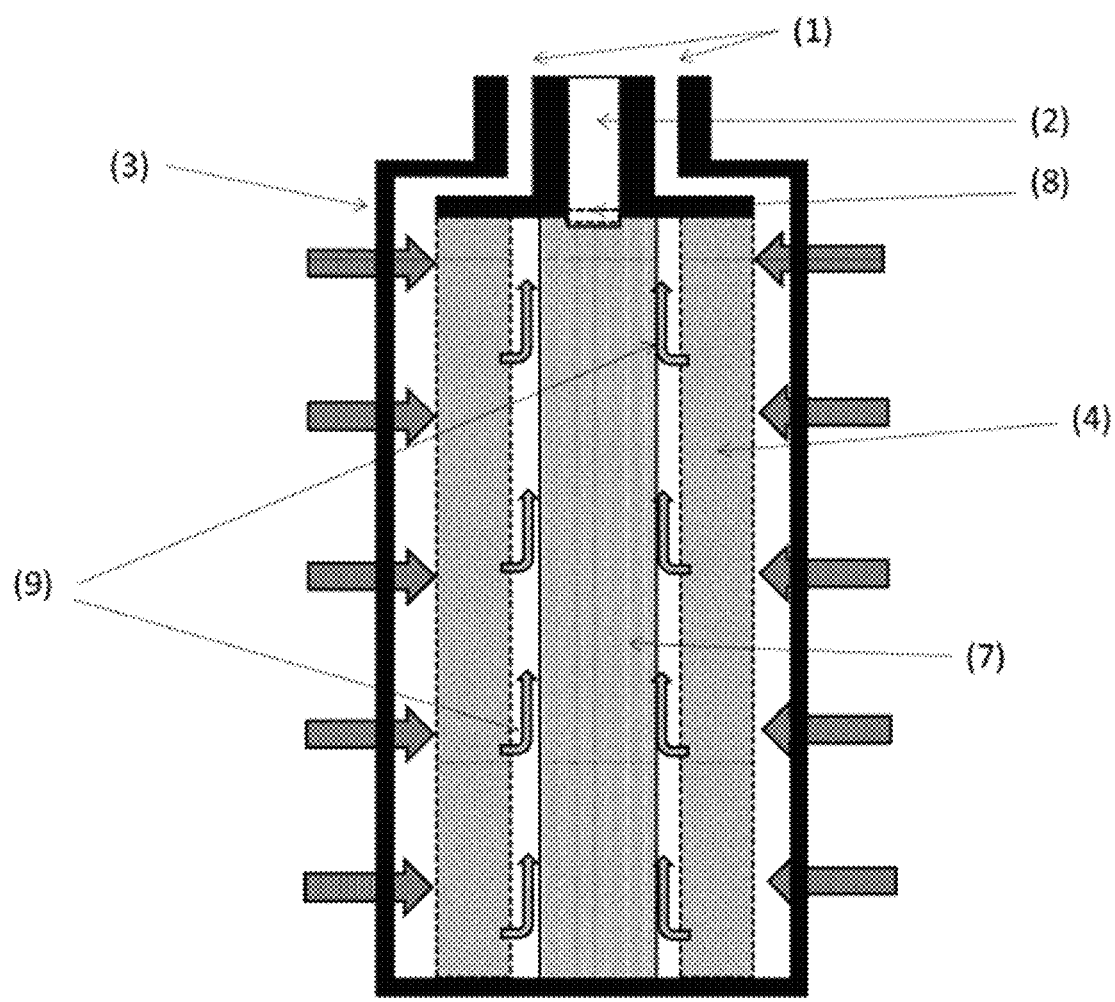
FIG. 6: Channel formation (bypassing) of the water to be filtered (9) in the case of a hollow fibre cartridge without a central drain with water inlet (1), water outlet (2), housing (3), hollow cylinder made of activated carbon (4), heavy metal-binding chelating resins and/or bacteria-removing resin as filling (7), frit (8) and channel formation (bypassing) (9),(6).

In the case of a filled hollow cylinder with a simple drain on one side of the cylinder, channels can additionally form at the wall of the inflow (7) (FIG. 6) which also prevent a flow through the absorber particles and lead to no or too low a depletion of the contaminants due to insufficient contact between water and absorber.

Figure 7:
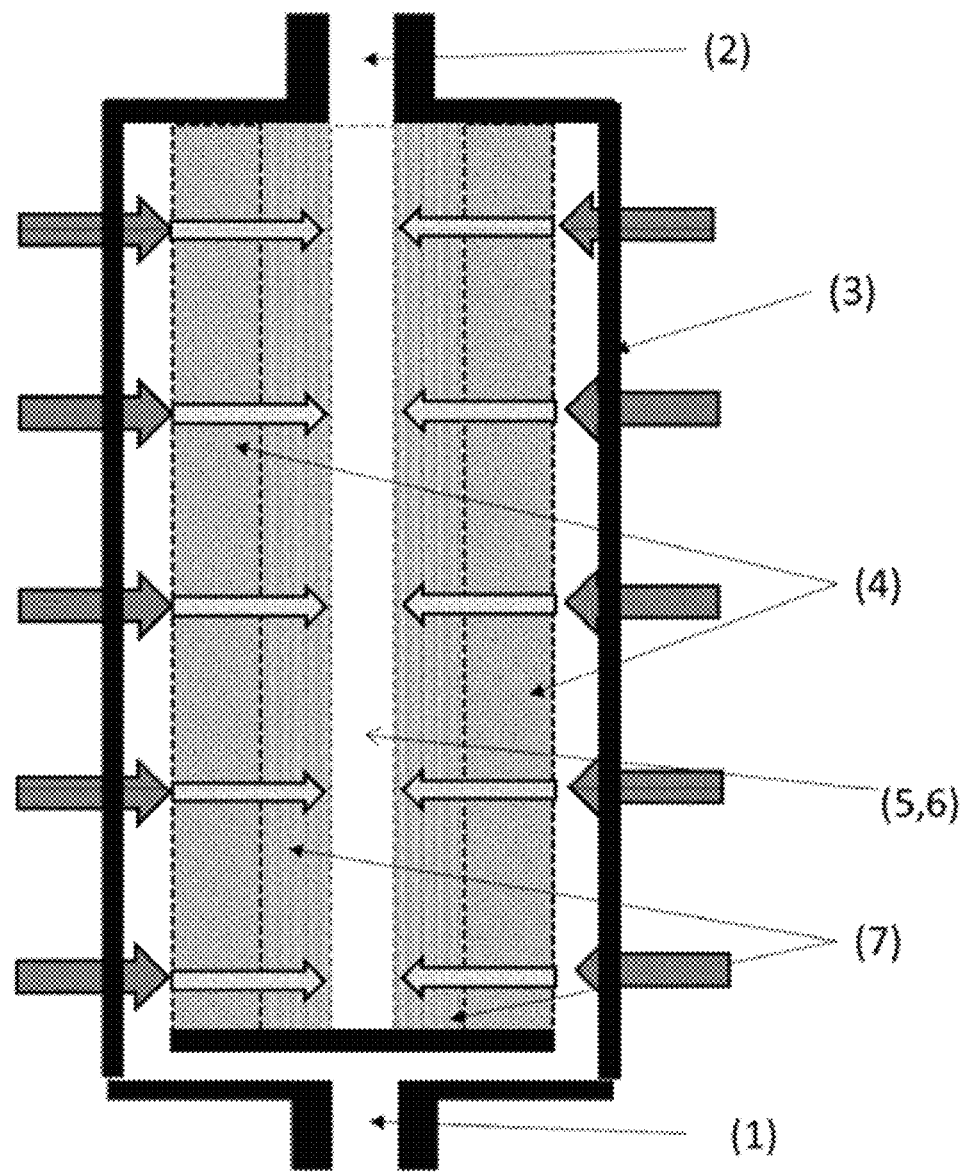
FIG. 7: Advantageous filtration path in the case of a filled hollow cylinder with a central drain and linear structure with inlet (2) and outlet (2) lying opposite each other; water inlet (1), water outlet (2), housing (3), hollow cylinder made of activated carbon (4), hollow cylinder with a permeable wall or hollow fibre membranes (5,6), heavy metal-binding chelating resins and/or bacteria-removing resin as filling (7).
Figure 8:
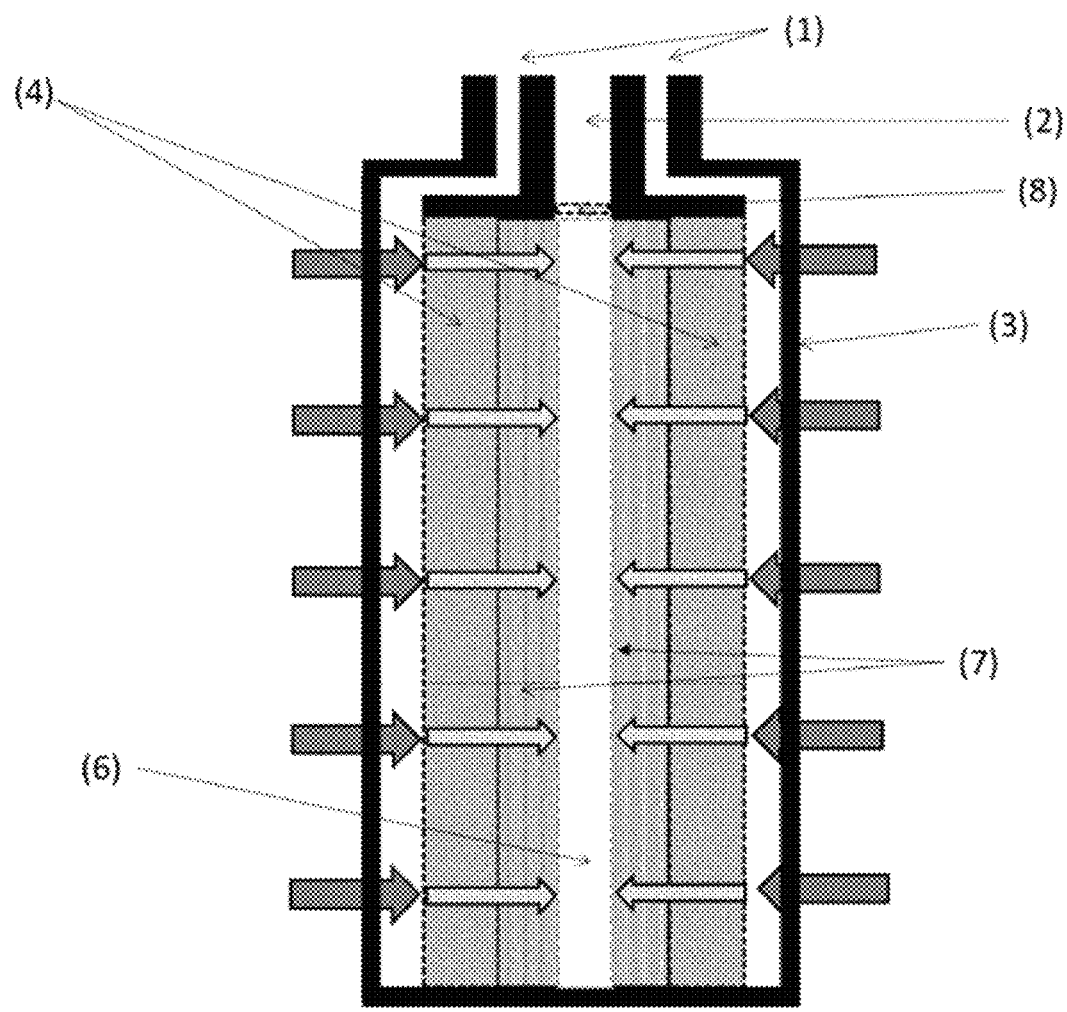
FIG. 8: Advantageous filtration path of a hollow cylinder with inlet (1) and outlet (2) on the same side; water inlet (1), water outlet (2), housing (3), hollow cylinder made of activated carbon (4), (6) hollow cylinder with a permeable wall or hollow fibre membranes (5,6), heavy metal-binding chelating resins and/or bacteria-removing resin as filling (7), frit (8).

One alternative here provides the radial arrangement of the separating media (5) and (7), such as is already realized in commercially available hollow cylinders with activated carbon blocks, with a central drain (5) (FIG. 7 and FIG. 8). This setup allows high flow rates with a low back pressure, short separation distance and homogeneous, uniform and complete throughflow (8) at the same time as a sufficient residence time of the water in the absorber bed.

The drain can consist of a multiply perforated pipe (6) with correspondingly small openings which allow the filtered water to pass through without an appreciable pressure drop, but retain the resin.

In addition, the central pipe can be provided with multiple openings which are large relative to the particle diameter of the resin if it is additionally provided with a suitable filter cloth with a correspondingly small mesh size (6).

Furthermore, the central drain can be achieved by one or more (bundled) hollow fibre membranes which extend over the entire length of the cylinder (6).

The arrangement can be designed with inlet and outlet lying opposite each other for the linear installation in a pipeline (FIG. 7) or with only one connection for inlet and outlet for easy installation in a water purification machine (FIG. 8).

As a variant, a combined hollow cylinder can also be used, in which activated carbon and one or more absorber resins are pressed/stuck together in a suitable manner.

The quantities or volumes of activated carbon, absorber resin and the quantity and capacity of the central drain or of the membrane can be matched to the drinking water quality standards and combined in such a way that a maximum productivity and effectiveness of the purification is achieved with a minimized pressure drop.

This setup allows an adaptation to regional differences and drinking water markets while retaining the principle claimed here.

The claimed device combines at least two long-lived water purification processes in one cartridge, which cover an extremely wide range of possible drinking water contaminants ("chlorine", small organic molecules, pharmaceutical residues, heavy metals, bacteria, viruses, particles, etc.).

Here the purification elements are arranged such that an optimum throughflow (and thus an optimum water-absorber contact) is achieved with a reduced pressure drop.

This setup allows a high productivity (large face area and small particle diameters are possible) with maximum purification efficiency, which cannot be achieved with alternative setups.

At the same time, a compact unit with a minimal space requirement is achieved, which can be easily monitored by the consumer.

The combination of different (long-lived) purification techniques reduces the complexity during the construction and during the use of the corresponding machine (few to no pipes or adapters, only one to two connections, etc.).

A simple connection to a water tap (possibly via a flexible adapter) or the installation in corresponding water pipelines is also conceivable.

In spite of the outwardly linear structure, it involves a radial filtration with short filtration paths, a sufficient residence time of the water in the gel bed and a very simple structure.

The handling for the end user is made much simpler compared with a system constructed in a modular manner (change/monitoring of only one cartridge, instead of two or three); the same applies to production, trade, marketing, distribution, storage, etc.

In a preferred embodiment, the cartridge can be linearly installed in a water pipeline or via a single connection, such as is already commonly used on the market.

The device can be easily combined with all common further purification or storage modules, for example a subsequent tank for storing the purified water, or further purification techniques, such as UV disinfection (in a tank or on-line), redox filters, etc., or for further use in hot water production, $CO_2$ addition module for the production of carbonated water, any chlorination or addition of hydrogen peroxide for subsequent disinfection or preservation, addition of health-promoting ions, such as calcium and/or magnesium, etc.

The device does not influence or compromise the type of subsequent water withdrawal or water treatment.

The efficiency of the device can be monitored by suitable sensors at a suitable point, either at the withdrawal point or at the points between the individual modules. Suitable sensors are for example, but not exclusively, pH sensors, conductivity sensors, sensors for checking the bacteria concentration, ion-selective sensors, UV sensors, etc. A flow-through cell can measure the quantity of water processed.

In a preferred embodiment, the sensors are connected to a data processing system which monitors the functioning of the individual modules on the basis of the measured values and issues corresponding messages if the replacement or regeneration of a cartridge has to be effected. The modules can also be replaced with the aid of the sensors in a purely time-controlled or volume-controlled manner. Depending on the embodiment, the data processing system can initiate an automatic regeneration of the softening module or close a valve, in order to force the replacement of modules as a condition for further operation.

The data processing system can be programmed such that it issues a message in the case of exhaustion or errors, e.g. on a mobile communications device, email, SMS, instant message, etc., which makes the consumer aware of the need to change the cartridge.

In the smallest design, the device is suitable for domestic use and is geared to typical consumers. In larger designs, the device can also be used in apartment buildings, housing complexes, in restaurants, hospitals, on ships or other facilities with a demand for high-quality drinking water.

The cartridge itself, i.e. the outer housing (3), the water inlet opening (1), the water outlet opening (2), the outer hollow cylinder made of activated carbon (4) and the inner central hollow cylinder with a hollow fibre membrane bundle (6) or a permeable wall (6) are preferably made of plastic. The production is effected according to established injection-moulding processes or by 3D printing, or combinations thereof. A post-processing of individual elements, for example drilling holes, etc., is likewise provided. The hollow fibres themselves are usually composed of polyethersulfone (PES) polymers. However, they can also consist of other materials.

The invention claimed is:

1. Device for purifying drinking water in multiple stages by combining orthogonal purification techniques in one module,
   wherein the device comprises a housing, a water inlet opening, a water outlet opening, an outer hollow cylinder filled with activated carbon and an inner hollow cylinder with a semipermeable wall, wherein the device is designed as a double hollow cylinder cartridge,
   wherein the inner hollow cylinder comprises a chelating and/or a bactericidal gel for removing heavy metals and/or bacteria, and
   wherein the chelating gel or the bactericidal gel or both are packed between an outer hollow cylinder filled with activated carbon and a central drain over the entire length of the hollow cylinder.

2. Device according to claim 1, wherein the central drain consists of a multiply perforated pipe with openings.

3. Device according to claim 1, wherein the openings of the multiply perforated pipe are smaller than the particles of the absorber gel with a chelating and/or antibacterial action surrounding them.

4. Device according to claim 1, wherein that the central drain consists of a pipe, wrapped with a membrane, with openings that are larger than the particle diameter of the absorber gel with a chelating and/or antibacterial action surrounding them.

5. Device according to claim 1, wherein the membrane has pores that are smaller than the particle diameter of the absorber gel with a chelating and/or antibacterial action surrounding them.

6. Device according to claim 1, wherein the central drain consists of one or more hollow fiber membranes or a bundle of hollow fiber membranes.

7. Device according to claim 1, wherein the device comprises a pH sensor, conductivity sensor, UV sensor, or sensors for identifying bacteria.

8. Device according to claim 7, wherein the sensors issue a warning if values exceed or fall below defined limit values.

9. Device according to claim 1, wherein the device contains further elements.

10. Device according to claim 9, wherein the further elements are selected from a water tank, a softening system, a hot water production system, a system for (UV) disinfection, redox filters, a $CO_2$ addition unit or a chlorination unit.

11. Device according to claim 1, wherein the housing, the water inlet opening, the water outlet opening, the outer hollow cylinder and the inner central hollow cylinder with a permeable wall are produced by 3D printing.

* * * * *